United States Patent
Heni et al.

(10) Patent No.: US 10,642,021 B2
(45) Date of Patent: May 5, 2020

(54) ENDOSCOPE

(71) Applicant: KARL STORZ SE & Co. KG, Tuttlingen (DE)

(72) Inventors: Andreas Heni, Tuttlingen (DE); Stefan Zehnder, Tuttlingen (DE); Andreas Limberger, Tuttlingen (DE); Siegfried Hoefig, Tuttlingen (DE); Jean-Sebastien Samson, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 122 days.

(21) Appl. No.: 15/987,428

(22) Filed: May 23, 2018

(65) Prior Publication Data

US 2018/0341101 A1    Nov. 29, 2018

(30) Foreign Application Priority Data

May 23, 2017   (DE) .......................... 10 2017 111 306

(51) Int. Cl.
*G02B 23/24* (2006.01)
*A61B 1/00* (2006.01)
(Continued)

(52) U.S. Cl.
CPC .......... *G02B 23/2469* (2013.01); *A61B 1/002* (2013.01); *A61B 1/0011* (2013.01);
(Continued)

(58) Field of Classification Search
None
See application file for complete search history.

(56) References Cited

U.S. PATENT DOCUMENTS

| 3,818,902 A | 6/1974 | Kinoshita et al. |
| 4,491,385 A | 1/1985 | Imagawa et al. |
| (Continued) | | |

FOREIGN PATENT DOCUMENTS

| CN | 104188618 A | 12/2014 |
| DE | 3225452 A1 | 1/1983 |
| (Continued) | | |

OTHER PUBLICATIONS

Extended European Search Report dated Jan. 25, 2019 in corresponding application EP18173822.0.
(Continued)

*Primary Examiner* — Elmito Breval
(74) *Attorney, Agent, or Firm* — Muncy, Geissler, Olds & Lowe, P.C.

(57) ABSTRACT

An endoscope having an outer shaft member with a distal end forming a distal end of the endoscope and an optics member with a distal end. The optics member is located inside the outer shaft member. The optics member defines a viewing direction of the endoscope, the viewing direction being tilted relative to a longitudinal axis of the outer shaft member. The endoscope further has optical fibers comprising an optically transparent material and provided and conditioned for the transport of illumination light to the distal end of the endoscope. The endoscope further has a segment located between an outer surface region of the distal end of the optics member and an inner surface region of the distal end of the outer shaft member. The orientation of distal ends of the optical fibers is defined by the segment.

20 Claims, 5 Drawing Sheets

(51) Int. Cl.
*A61B 1/07* (2006.01)
*A61B 1/06* (2006.01)
*A61B 1/04* (2006.01)
*A61B 1/055* (2006.01)
*A61B 1/002* (2006.01)

(52) U.S. Cl.
CPC ...... *A61B 1/00096* (2013.01); *A61B 1/00179* (2013.01); *A61B 1/00193* (2013.01); *A61B 1/042* (2013.01); *A61B 1/055* (2013.01); *A61B 1/0623* (2013.01); *A61B 1/07* (2013.01); *G02B 23/2415* (2013.01); *G02B 23/2423* (2013.01); *G02B 23/2484* (2013.01)

(56) References Cited

U.S. PATENT DOCUMENTS

| | | |
|---|---|---|
| 4,576,147 A | 3/1986 | Hashiguchi |
| 4,850,342 A | 7/1989 | Hashiguchi et al. |
| 5,046,816 A | 9/1991 | Lehmann et al. |
| 5,305,736 A | 4/1994 | Ito |
| 5,700,236 A | 12/1997 | Sauer et al. |
| 5,718,664 A | 2/1998 | Peck et al. |
| 7,569,013 B2 | 8/2009 | Scherr |
| 7,662,096 B2 | 2/2010 | Renner et al. |
| 9,297,954 B2 | 3/2016 | Dahmen |
| 9,964,752 B2 | 5/2018 | Buerk |
| 2005/0250992 A1 | 11/2005 | Scherr |
| 2015/0094539 A1 | 4/2015 | Eisenkolb |
| 2015/0351629 A1* | 12/2015 | Wheatley ............ G01B 9/0205 600/425 |
| 2017/0035282 A1 | 2/2017 | Kaneko |
| 2017/0095142 A1 | 4/2017 | McDowall |
| 2017/0261742 A1 | 9/2017 | Wieters et al. |

FOREIGN PATENT DOCUMENTS

| | | |
|---|---|---|
| DE | 3929285 A1 | 3/1991 |
| DE | 10027477 A1 | 12/2001 |
| DE | 10307903 A1 | 9/2004 |
| DE | 102004023024 A1 | 12/2005 |
| DE | 102011007878 A1 | 10/2012 |
| DE | 102012200794 A1 | 7/2013 |
| DE | 102013112282 A1 | 1/2014 |
| DE | 102014111069 A1 | 2/2016 |
| DE | 102014113352 A1 | 3/2016 |
| EP | 0898184 A2 | 2/1999 |

OTHER PUBLICATIONS

Partial European Search Report dated Nov. 12, 2018 in corresponding application 18173822.0.

* cited by examiner

ENDOSCOPE

This nonprovisional application claims priority under 35 U.S.C. § 119(a) to German Patent Application No. 10 2017 111 306.1, which was filed in Germany on May 23, 2017, and which is herein incorporated by reference.

BACKGROUND OF THE INVENTION

Field of the Invention

The present invention relates to an endoscope and a method of manufacturing an endoscope. In particular, the present invention defines a predetermined orientation of distal ends of optical fibers in the endoscope.

Description of the Background Art

In DE 32 25 452 A1, EP 0 898 184 A2, DE 10 2011 007 878 A1, sheaths holding ends of optical fiber bundles are described.

In U.S. Pat. No. 3,818,902, an endoscope 2 having an illumination window 6 is described (column 2, lines 10 through 12; FIG. 1). An end face of a bundle 10 of optical fibers constituting an illumination optical system is bonded to the back side of the illumination window 6 (column 2, lines 14 through 17).

In U.S. Pat. No. 4,576,147, a rigid endoscope 11 comprising in inner tube 17 eccentrically arranged within an outer tube 18 is described (column 3, lines 7 and 8, lines 17 and 18; FIG. 4). Distal ends of light guide fibers 21 are arranged in a substantially meniscus-shaped space between a hemispherical tip member 20 of the inner tube 17 and the outer tube 16 (column 3, lines 20 through 25).

A similar endoscope is described in U.S. Pat. No. 4,850,342.

In DE 39 29 285 A1, which corresponds to U.S. Pat. No. 5,046,816, an endoscope comprising an outer tube 3 and an inner tube 4 is described (column 2, lines 26 through 30). The inner tube 4 contains optical elements. Optical fibers 8 for the transmission of illumination light are arranged in the space between the outer tube 3 and the inner tube 4 (column 2, lines 37 through 39). Bars or walls 6 between the outer tube 3 and the inner tube 4 subdivide the space between the tubes 3, 4 and cause a parallel arrangement of the tubes 3, 4 and of the optical fibers 8.

In U.S. Pat. No. 5,305,736, a distal end part of an endoscope is described. A distal end block 1 provides a bore 33 (column 5, line 3; FIG. 3). An exit end portion 30a of a light guide fiber bundle 30 is inserted into a metallic pipe 32 which is arranged in the bore 33 (column 4, lines 67, through column 5, line 2).

In U.S. Pat. No. 5,700,236, an endoscope sheath 10 for changing angle of view is described (column 1, lines 12 through 14; column 3, lines 65 through 67; FIG. 1). A curved fiber bundle 18; 76 is provided in a distal end portion 22 of an elongated sheath portion 14 or member 72 (column 5, lines 46 through 48; column 6, lines 23 through 27; FIG. 4; column 8, lines 48 through 51; FIG. 17).

In U.S. Pat. No. 5,718,664, a disposable arthroscope 100 having an inclined angle of view is described (column 4, line 7). Illumination fibers 510 are arranged in a space between an outer tube 310 and an inner liens tube 320. A shim 330 serves as a guide to position the end portions of each illumination fibers 510 at a desired orientation (column 5, lines 45 through 46).

In DE 100 27 477 A1, preconfiguration of an optical fiber strand for an endoscope is described (paragraph [0006]). The optical fiber bundle is placed in an appropriate mould, the distal end of the optical fiber bundle is oriented according to the viewing direction, and the entire optical fiber bundle is fused together.

In DE 103 07 903 A1, which corresponds to U.S. Pat. No. 7,662,096 and which is incorporated herein by reference, an endoscope 10 comprising an outer tube 18, an inner tube 20 containing image transferring rod lenses 22 and an optical fiber bundle 30 is described (paragraphs [0063], [0064], [0065], FIGS. 1, 2). The optical fiber bundle 30 is located inside a flexible hose 28 in the space between the outer tube 18 and the inner tube 20 (paragraphs [0064], [0065], FIG. 1).

In DE 10 2004 023 024 A1 (also published as US 2005/0250992 A1), an endoscope comprising an outer tube 2 and a fiber tube 3 is described (paragraph [0027], FIG. 1). Subgroups 12 and 13 of optical fibers 11 are arranged in three compartments 9 and 10, respectively, of a space between the outer tube 2 and the fiber tube 3. Inclined surface areas 15, 16 at the fiber tube 3 are parallel to the viewing direction (paragraphs [0028], [0029], FIG. 5) and determine the orientation of the distal ends of the optical fibers 11 (paragraph [0011]).

In DE 10 2012 200 794 A1, which corresponds to U.S. Pat. No. 9,297,954, which is incorporated herein by reference, a formation of a light guide 1 is provided that comprises a flexible section 3 and a curved section 4 (paragraph [0039], FIG. 1). In the curved section 4, light guiding fibers 6 of the light guide 1 are agglutinated by means of a cured adhesive 8 (paragraph [0042]).

In DE 10 2013 112 282 A1, an endoscope 10 is described. Distal ends of light guide fibers 24 are arranged in an opening 82 in a distal face member 80.

In CN 104188618 A, a front end structure of a 3D-endoscoppe is described (abstract, paragraph [0006], claim 1). The front end structure comprises a fixing plate 2 with holes 2-1 for the two optical channels and holes for optical fibers, the latter comprising crescent shapes (paragraphs [0006], [0008], FIG. 1).

In DE 10 2014 111 069 A1, which corresponds to US 2017/0261742, an endoscope 10 with a fiber tube 11 and an outer tube 12 is described (paragraph [0027], FIG. 1). A distal end region 18 of an optical fiber bundle 17 is arranged in an opening 27 in the distal end of the fiber tube 11 (paragraph [0033], Figures).

In DE 10 2014 113 352 A1 (also published as WO 2016/041637 A1), an endoscope 10 comprising a fiber tube 14 arranged within an outer tube 15 is described (paragraph [0029], FIG. 1). A fiber bundle 18 comprising a number of optical fibers 17 is arranged in a space 16 between the fiber tube 14 and the outer tube 15 (paragraph [0030]). Distal ends of the optical fibers 17 are held by a sheath 19 (paragraph [0030], FIG. 2).

In US 2017/0035282 A1, an endoscope 10 is described (paragraph [0029], FIG. 1). Distal end portions 61p of first fibers 61 and distal end portions 62p of second fibers 62 are held by pipes 70 (paragraphs [0045], [0047], [0048]).

SUMMARY OF THE INVENTION

It is therefore an object of the present invention to provide an improved endoscope and an improved method of manufacturing an endoscope wherein the distal ends of optical fibers guiding illumination light are held in a predetermined orientation.

In an exemplary embodiment, an endoscope is provided that comprises an outer shaft member with a distal end forming a distal end of the endoscope; an optics member with a distal end, the optics member being located inside the outer shaft member, the optics member defining a viewing direction of the endoscope, the viewing direction being tilted relative to a longitudinal axis of the outer shaft member; optical fibers comprising an optically transparent material and provided and conditioned for the transport of illumination light to the distal end of the endoscope; and a segment located between an outer surface region of the distal end of the optics member and an inner surface region of the distal end of the outer shaft member, wherein the orientation of distal ends of the optical fibers is defined by the segment.

The endoscope can be a medical endoscope facilitating microinvasive diagnostic, therapeutic or other surgical measures or procedures or a technical endoscope (sometimes also referred to as borescope) for the inspection of cavities in turbines or other machines or for other technical applications. A shaft of the endoscope may be partially or completely rigid and/or partially or completely flexible.

In particular, the outer shaft member forms the outer surface of the shaft of the endoscope. In particular, the outer shaft member is tubular; in other words, the outer shaft member provides the shape of the lateral surface of a cylinder with a circular cross section or with any other cross section.

In particular, the optics member comprises a tubular inner shaft member providing the shape of a lateral surface of a cylinder with a circular cross section or any other cross section. In particular, the optics member comprises an objective or one or more lenses collecting light emanating from an object and focusing the light to an image plane thereby forming an image of the object.

The optics member can comprise a series of rod lenses or any other relay lens system relaying that image. The optics member can comprise an image sensor or a camera converting an optical image to an analogue or digital electronic signal representing the optical image. For instance, such image sensor can be located at the distal end of the endoscope, the image sensor directly capturing the optical image produced by an objective or one or more lenses. As an alternative, such image sensor can be located at the proximal end, the image sensor capturing the optical image relayed by a relay lens system or by a bundle of optical fibers.

In particular, the optics member comprises a window element made of an optically transparent material at its distal end. In particular, the rim of the window element is soldered or welded or otherwise hermetically tightly joined to the distal edge of the tubular inner shaft member.

In particular, the viewing direction of the optics member is the optical axis of an objective or a lens of the optics member. In Particular, the viewing direction is orthogonal to a light entrance surface (in particular formed by the window element described above) of the optics member. The viewing direction is not parallel to a longitudinal axis of the outer shaft member, in case of a curved or flexible outer shaft member: to the longitudinal axis of the distal end of the outer shaft member.

In particular, the proximal ends of the optical fibers are located at a proximal end of the endoscope. The optical fibers can be provided and conditioned to transport or guide illumination light produced by a light source at the proximal end of the endoscope. As an alternative, illumination light produced by an external light source can be transported or guided to the proximal end of the endoscope by means of a fiber-optical cable and transported or guided from the proximal end to the distal end of the endoscope by means of the optical fibers.

Surfaces of the optical fibers at their distal ends form light emitting surfaces emitting illumination light guided by the optical fibers. Illumination light guided by the optical fibers and emitted at their distal ends can illuminate an object to be viewed by the endoscope.

The endoscope differs from the endoscope described in DE 10 2014 111 069 A1 in that a segment is provided which segment is not identical to the distal end of the optics member. The segment is originally fabricated separate from the optics member and is joined to the optics member and to other parts of the endoscope at a late moment in the manufacturing process of the endoscope.

Providing the segment or a number of segments located between the outer surface region of the distal end of the optics member and an inner surface region of the distal end of the outer shaft member can make the manufacture of the endoscope easier and/or can provide additional flexibility in the design of the endoscope.

In an endoscope as described herein, a distal front face of the endoscope is, in particular, tilted, wherein the edge of the distal front face of the endoscope provides a most distal region and a most proximal region, and wherein the distal ends of the optical fibers are located between the distal end of the optics member and the most proximal region of the edge of the distal front face of the endoscope.

All the conventional endoscopes with tilted viewing direction described in U.S. Pat. Nos. 4,576,147, 4,850,342, DE 39 29 285 A1, U.S. Pat. Nos. 5,700,236, 5,718,664, DE 100 27 477 A1, DE 10 2004 023 024 A1, DE 10 2013 112 282 A1, DE 10 2014 111 069 A1, DE 10 2014 113 352 A1 provide distal ends of optical fibers guiding illumination light at the most distal region of the edge of the distal front face of the endoscopes only. At most, the distal ends of the optical fibers are distributed within a sickle-shaped area. None of the conventional endoscopes provides distal ends of optical fibers at the most proximal region of the edge of the distal front face.

In an endoscope as described herein, a distal front face of the endoscope is, in particular, tilted relative to the longitudinal axis o the outer shaft member, wherein the edge of the distal front face of the endoscope provides a most distal region and a most proximal region, and wherein the segment is located between the distal end of the optics member and the most proximal region of the edge of the distal front face of the endoscope.

In an endoscope as described herein, a distal front face of the endoscope is, in particular, tilted relative to the longitudinal axis o the outer shaft member, wherein the edge of the distal front face of the endoscope provides a most distal region and a most proximal region, and wherein the entire segment is located between the distal end of the optics member and the most proximal region of the edge of the distal front face of the endoscope.

The entire segment being located between the distal end of the optics member and the most proximal region of the edge of the distal front face of the endoscope means that no part of the segment is located between the distal end of the optics member and the most distal region of the edge of the distal front face of the endoscope. Another segment can be located between the distal end of the optics member and the most distal region of the edge of the distal front face of the endoscope.

In particular, an endoscope as described herein further comprises further optical fibers comprising an optically transparent material and provided and conditioned for the transport of illumination light to the distal end of the endoscope, wherein distal ends of the further optical fibers are located between the distal end of the optics member and the most distal region of the edge of the distal front face of the endoscope.

With illumination light emanating from distal ends of optical fibers located both close to the most distal region and close to the most proximal region of the edge of the distal front face, a particularly homogeneous illumination of objects to be viewed by the endoscope is facilitated. In particular, shadows can be reduced and viewing objects by means of the endoscope can be more comfortable for medical personal.

In particular, in an endoscope as described herein, the distal end of the optics member at least one of directly abuts on and is directly joined to the distal end of the outer shaft member.

In particular, the distal end of the optics member is bonded to the inner surface of the distal end of the outer shaft member by an adhesive or a casting or sealing compound.

In particular, in an endoscope as described herein, the distal end of the optics member at least one of directly abuts on and is directly joined to two separate regions of the inner surface of the distal end of the outer shaft member, wherein these two regions are located opposite to each other.

In particular, these two regions are located opposite to each other with respect to the center or the axis of symmetry of the distal end of the outer shaft member.

In particular, an endoscope as described herein is a stereo-endoscope comprising two optical paths for the capture of two pictures facilitating binocular vision.

In particular, the two or more optical paths of the endoscope are similar to each other. In particular, the two or more optical paths of the endoscope are parallel to each other.

In particular, a stereo-endoscope as described herein comprises two optics members arranged in parallel, each optics member providing one of the optical paths, wherein the distal end of each optics member at least one of directly abuts on and is directly joined to the distal end of the outer shaft member.

In particular, the two optics members are similar and provide identical characteristics. In particular, the two optics members directly abut on and/or are directly joined to two regions of the inner surface of the outer shaft member. These two regions can be arranged at opposite sides of the outer shaft member.

Each optics member directly abutting on inner surface regions of the distal end of the outer shaft member allows for maximum cross sections of both optics members. Thus, an optimum quality of images captured by the endoscope can be achieved.

In particular, in an endoscope as described herein, the segment does not completely surround the distal end of the optics member.

For instance, the segment is merely provided between two separate regions in which the optics member or the optics members abut on the inner surface of the outer shaft member. When the segment does not completely surround the distal end of the optics member or the optics members, the cross section of the optics member or the cross sections of the optics members can be maximum.

In particular, in an endoscope as described herein, adhesive or solder or a sealing or casting compound or a weld or a crimp joins the segment to at least one of the outer surface region of the distal end of the optics member and the inner surface region of the distal end of the outer shaft member.

In particular, adhesive or solder or a sealing or casting compound joins the segment both to the outer surface region of the distal end of the optics member and to the inner surface region of the distal end of the outer shaft member.

The segment and the optical fibers and the distal end of the optics member and the distal end of the outer shaft member can be joined together simultaneously by the same material and in the same procedural step. Thereby, manufacture of the endoscope is simplified.

In particular, in an endoscope as described herein, the segment comprises a through hole accommodating the distal ends of the optical fibers.

The direction or axis of symmetry of the through hole or, more general, the orientation of the wall of the through hole defines the direction of the distal ends of the optical fibers and, thereby the direction in which illumination light is emitted.

In particular, in an endoscope as described herein, the orientation of the through hole defines the orientation of the distal ends of the optical fibers, the orientation of the through hole being tilted relative to the longitudinal axis of the endoscope.

In particular, the orientation of the through hole is parallel to the viewing direction of the endoscope.

The segment can comprise a number of through holes.

A method of producing an endoscope comprises steps of providing a segment comprising a through hole, threading optical fibers through the through hole in the segment, joining the segment to a distal end of an optics member, wherein an axis of symmetry of the through hole is tilted with respect to a longitudinal axis of the optics member, and inserting the entity comprising the optics member and the segment into an outer shaft member.

In particular, in a method as described herein, the entity comprising the optics member and the segment is inserted into an outer shaft member from a proximal end of the outer shaft member to a distal end of the outer shaft member.

A method of manufacturing an endoscope comprises steps of providing a segment work piece with a through hole, threading optical fibers through the through hole in the segment work piece, inserting an optics member into an outer shaft member of the endoscope and inserting the segment work piece into the outer shaft member.

In particular, a method of manufacturing as described herein further comprises a step of threading the optical fibers through the outer shaft member of the endoscope before or after threading the optical fibers through the through hole in the segment work piece.

The steps of inserting the optics member and inserting the segment work piece can be conducted in this order. As an alternative, the optics member can be inserted after the segment work piece is inserted. As a further alternative, both the optics member and the segment work piece can be inserted into the outer shaft member simultaneously.

In particular, in a method as described herein, the optics member is inserted into the outer shaft member in a first direction from a proximal end of the outer shaft member to the distal end of the outer shaft member and the segment work piece is inserted into the outer shaft member in a second direction opposite to the first direction.

In particular, a method as described herein further comprises a step of simultaneously joining the segment work piece to an outer surface region of a distal end of the optics member and to an inner surface region of a distal end of the outer shaft member.

In particular, a method as described herein further comprises a step of removing a region of the segment work piece protruding from the distal end of the outer shaft member.

As an alternative, the segment work piece can be identical to the segment. In this case, there is no need to modify the segment work piece after it is inserted into the outer shaft member.

A method as described herein can be applied for the manufacture of an endoscope as described herein. The methods described herein can be modified in order to generate the features, characteristics and functions of endoscopes as described herein.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
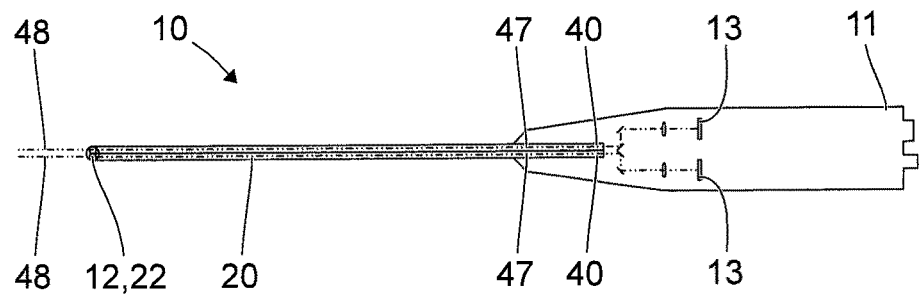
FIG. 1 shows a schematic representation of an endoscope.

FIG. 1 shows a schematic representation of a stereoscopic endoscope 10 with a proximal end 11 and a distal end 12. The proximal end 11 is part of a handle comprising two image sensors 13. The endoscope 10 comprises a thin straight rigid cylindrical shaft 20 with a distal end 22 forming the distal end 12 of the endoscope 10.

Two similar optics members 40 are arranged in parallel in the shaft 20. In the simplified representation of FIG. 1, each optics member is merely represented by a tubular inner shaft member. The inner shaft member of each optics member 40 contains an objective or one or more lenses and one or more prisms at the distal end 12 of the endoscope 10 and a number of rod lenses or another kind of relay lens system.

The objective or the lens or lenses and the relay lens system of each optics member 40 are arranged in rotational symmetry to a respective optical axis 47, 48. In FIG. 1, optical paths of the respective optics member 40 are schematically represented by the respective optical axes 47, 48 of the optical elements of each optics member 40.

The optical paths comprise mirrors or reflective interfaces of prisms or other optical elements folding or bending the optical paths and their optical axes. In particular, reflective interfaces (schematically represented by short oblique lines in FIG. 1) are arranged between the proximal end of each optics member 40 and the respective image sensor 13.

Further reflective interfaces in FIG. 1 can be arranged at the distal end of each optics member 40. These reflective interfaces at the distal ends of the optics members 40 fold or bend the optical axes 47, 48. Therefore, the optical axes 48 distal to the distal ends of the optics members 40 are not parallel to the optical axes 47 proximal to the distal ends of the optics members 40. However, the plane of projection of FIG. 1 is orthogonal to the planes defined by both parts 47, 48 of the optical axis of each optics member 40.

The optical axes 48 distal to the distal ends of the optics members 40 define the viewing directions of the respective optics members 40. The viewing directions 48 of both optics members 40 are parallel.

Figure 2:
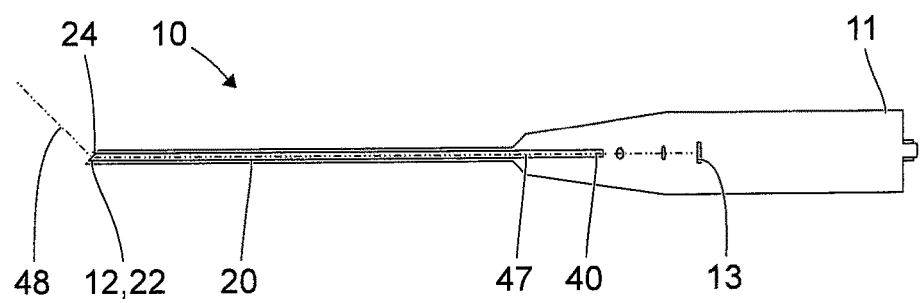
FIG. 2 shows a further schematic representation of the endoscope shown in FIG. 1.

FIG. 2 shows another schematic representation of the endoscope 10 described above with reference to FIG. 1. The plane of projection of FIG. 2 is orthogonal to the plane of projection of FIG. 1.

The distal end 22 of the shaft 20 of the endoscope 10 comprises a distal front face 24. This distal front face 24 is orthogonal to the plane of projection of FIG. 2 and tilted with reference to the longitudinal axis of the shaft 20 (in the example shown in FIG. 2: by about 45 degrees). In the example shown in FIGS. 1 and 2, the optical axes 48 distal to the distal ends of the optics members 40—also defining the viewing directions of the respective optics members 40—are orthogonal to the distal front face 24 of the shaft 20.

Figure 3:
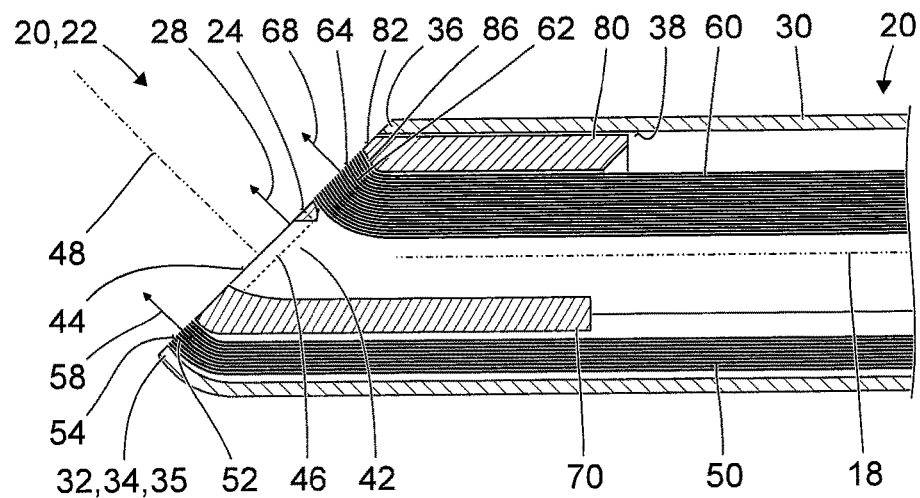
FIG. 3 shows a schematic representation of a section through the distal end of the endoscope shown in FIGS. 1 and 2.

FIG. 3 shows a schematic representation of a section of the distal end 22 of the shaft 20 of the endoscope 10 described above with reference to FIGS. 1 and 2. The sectional plane of FIG. 3 is parallel to the plane of projection of FIG. 2 and parallel to the optical paths 47, 48 of the optics members 40.

The outer surface of the shaft 20 is formed by an outer shaft member 30. In the example described with reference to FIGS. 1 through 3, the outer shaft member 30 provides the shape of a lateral surface of a cylinder with circular cross section. The axis 18 of rotational symmetry of the outer shaft member 30 is the longitudinal axis of the shaft 20 of the endoscope.

The angle by which the distal front face 24 of the shaft 20 is tilted with respect to the longitudinal axis 18 of the shaft 20 equals the angle by which the optical axes 47, 48 of the optics members 40 are bent. Therefore, the normal vector 28 of the distal front face 24 of the shaft 20 is parallel to the optical axes 48 of the optics members 40 distal to the distal front face 24 of the shaft 20.

The distal end 32 of the outer shaft member 30 is formed by a distal edge 34. The distal edge 34 of the outer shaft member 30 is nearly elliptical. The distal edge 34 of the outer shaft member 30 is the edge of the distal front face 24 of the shaft 20. Since the distal front face 24 of the shaft 20 is tilted with respect to the longitudinal axis 18 of the shaft 20, the distal edge 34 provides a most distal region 35 and a most proximal region 36.

In the outer shaft member 30, the optics members 40 are arranged in mirror symmetry with respect to the sectional plane of FIG. 3. Therefore, one optics member 40 is arranged behind the sectional plane of FIG. 3 and (partially) visible in FIG. 3. While other components of the optics member 40 are not represented in FIG. 3, a window member 46 forming a light inlet surface 44 at the distal end 42 of the optics member is represented by a dotted line in FIG. 3. The light inlet surface 44 at the distal end 42 of the optics member 40 is part of the distal front face 24 of the shaft 20.

The endoscope comprises a bundle of first optical fibers 50. Distal ends 52 of the optical fibers 50 are arranged next to the most distal region 35 of the edge 34 of the outer shaft member 30. Light emitting surfaces 54 at the distal ends 52 of the first optical fibers 50 are part of the distal front face 24 of the shaft 20. A normal vector 58 of the light emitting surfaces 54 (which is, by definition, orthogonal to the light emitting surfaces 54) is parallel to the normal vector 28 of the entire distal front face 24.

The endoscope comprises a bundle of second optical fibers 60. Distal ends 62 of the second optical fibers 60 are arranged close to the most proximal region 36 of the distal edge 34 of the outer shaft member 30. Light emitting surfaces 64 at the distal ends 62 of the second optical fibers 60 art part of the distal front face 24 of the shaft 20. A normal vector 68 of the light emitting surfaces 64 of the second optical fibers 60 is parallel to the normal vector 28 of the entire distal front face 24.

The endoscope comprises a first segment 70 at the distal end 22 of the shaft 20. The sectional plane of FIG. 3 intersects the first segment 70. A distal region 72 of the surface of the first segment 70 is part of the distal front face 24. The first segment 70 is arranged between the bundle of first optical fibers 50 and the optics members 40. In the sectional representation shown in FIG. 3, part of the distal end 42 of the optics member 40 is covered by the first segment 70 and, therefore, not visible.

The endoscope comprises a second segment 80 at the distal end 22 of the shaft 20. The sectional plane of FIG. 3 intersects the second segment 80. A distal region 82 of the outer surface of the second segment 80 forms part of the distal front face 24 of the shaft 20. The second segment 80 comprises a through hole 86 accommodating the distal ends 60 of the second optical fibers 60. The distal region 82 of the outer surface of the second segment 80 provides the topology of a circle and encloses the through hole 86 and the light emitting surfaces 64 of the second fibers 60.

In the section view of FIG. 3, parts of the optics member 40 and of the second segment 80 are covered by the second optical fibers 60. In a region covered by the second optical fibers 60, the second segment 80 abuts on and is joined by an adhesive to the optics member 40. Furthermore, the second segment 80 abuts on and is joined to an inner surface region 38 of the outer shaft member 30.

Figure 4:
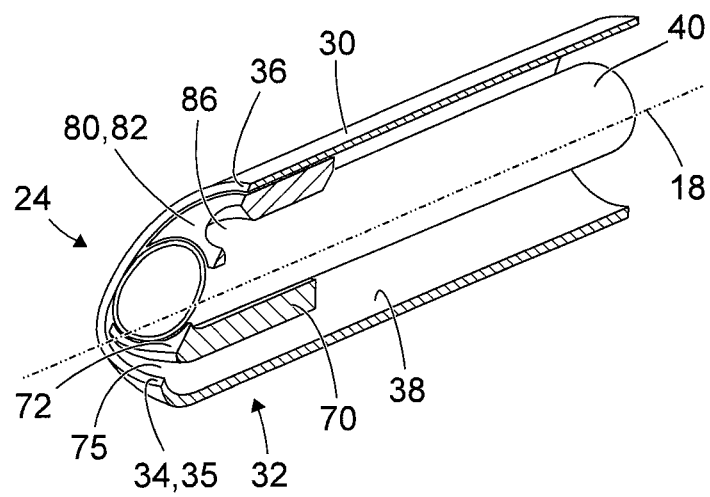
FIG. 4 shows a schematic axonometric sectional view of the distal end shown in FIG. 3.

FIG. 4 shows a schematic axonometric sectional view of the shaft's 20 distal end 22 described above with reference to FIG. 3. The sectional plane of FIG. 4 is the sectional plane of FIG. 3. In contrast to FIG. 3, the shaft 20 is shown without optical fibers 60, 80 (confer FIG. 3).

In the distal end face 24 of the endoscope 20, there is a gap 75 between the most distal region 35 of the distal edge 34 of the outer shaft member 30 and the distal region 72 of the surface of the first segment 70. In the complete endoscope (as described above with reference to FIGS. 1 through 3), light emitting surfaces 64 at the distal ends 62 of the second optical fibers 60 are arranged in the gap 75.

The shape of part of the surface of the first segment 70 corresponds to the shape of the lateral surface of the optics member 40. Solder or an adhesive or a weld joins the corresponding surface areas of the optics member 40 and the first segment 70. The entire arrangement (one half of which is displayed in FIG. 4) comprises two parallel optics members 40 both joined to the same first segment 70. Thus, the first segment 70 rigidly connects the distal ends 42 of the optics members 40 to each other.

As can be seen in FIG. 4, the optics members 40 directly abut on (and in particular are joined to by means of solder or an adhesive or a weld) to the inner surface 38 of the outer shaft member 30. Both segments 70, 80 are arranged at opposite sides of the optics members 40. There is no direct mechanical contact between the segments 70, 80. Rather, both segments 70, 80 are arranged in different and separate compartments between the outer shaft member 30 and the optics members 40. The distal region 72 of the surface of the first segment 70 is arranged close to the most distal region 35 of the edge 34 of the outer shaft member 30. The distal region 82 of the outer surface of the second segment 80 is arranged next to the most proximal region 36 of the distal edge 34 of the outer shaft member 30.

Figure 5:
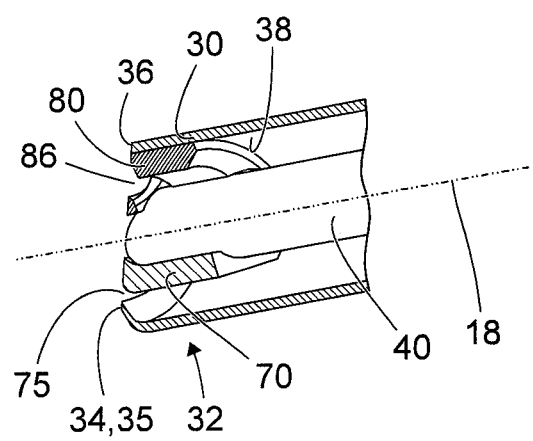
FIG. 5 shows a further schematic axonometric sectional view of the distal end shown in FIGS. 3 and 4.

FIG. 5 shows another schematic axonometric sectional view of the distal end 22 of the shaft 20 of the endoscope described above with reference to FIGS. 1 through 4. The sectional plane of FIG. 5 is the sectional plane of FIGS. 3 and 4. The viewing direction of FIG. 5 is different from the viewing direction of FIG. 4.

A concavely curved recess 85 of the second segment 80 forms a channel between the optics members 40 and the second segment 80. This channel is provided for accommodating the second optical fibers 60 (confer FIG. 3). The distal end of the concavely curved recess 85 continues to the through hole 86.

Figure 6:
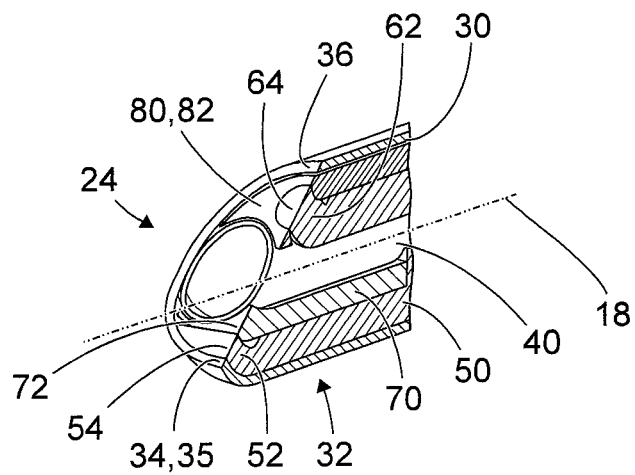
FIG. 6 shows a further schematic axonometric sectional view of the distal end shown in FIGS. 3 through 5.

FIG. 6 shows another schematic axonometric sectional view of the distal end 22 of the shaft 20 of the endoscope described above with reference to FIGS. 1 through 5. The sectional plane of FIG. 6 is the sectional plane of FIGS. 3 through 5. The viewing direction of FIG. 6 is similar to the viewing direction of FIG. 4. In contrast to FIGS. 4 and 5, optical fibers 50, 60 are shown in FIG. 6.

The first optical fibers 50 are arranged between the first segment 70 and the outer shaft member 30. The second optical fibers 60 are arranged between the optics members 40 and the second segment 80 and in the through hole 86 in the second segment 80.

Figure 7:
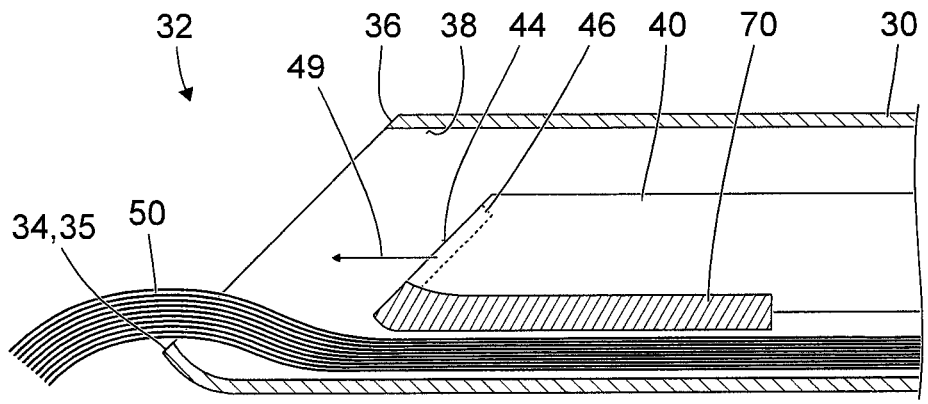
FIG. 7 shows a further schematic representation of a section through the distal end shown in FIGS. 3 through 6.

FIG. 7 shows a schematic sectional representation of components of the distal end 22 of the shaft 20 described above with reference to FIGS. 1 through 6 during manufacture. The sectional plane of FIG. 7 is the sectional plane of FIGS. 3 through 6.

In the situation or configuration shown in FIG. 7, both optics members 40 are joined to the first segment 70. The first optical fibers 50 are threaded through the outer shaft member 30. Distal ends of the first optical fibers 50 are distal of the distal edge 34 of the outer shaft member 30. The assembly comprising the optics members 40 and the first segment 70 is inserted into the outer shaft member 30 in a first direction 49 from a proximal end to the distal end 32 of the outer shaft member 30.

Figure 8:
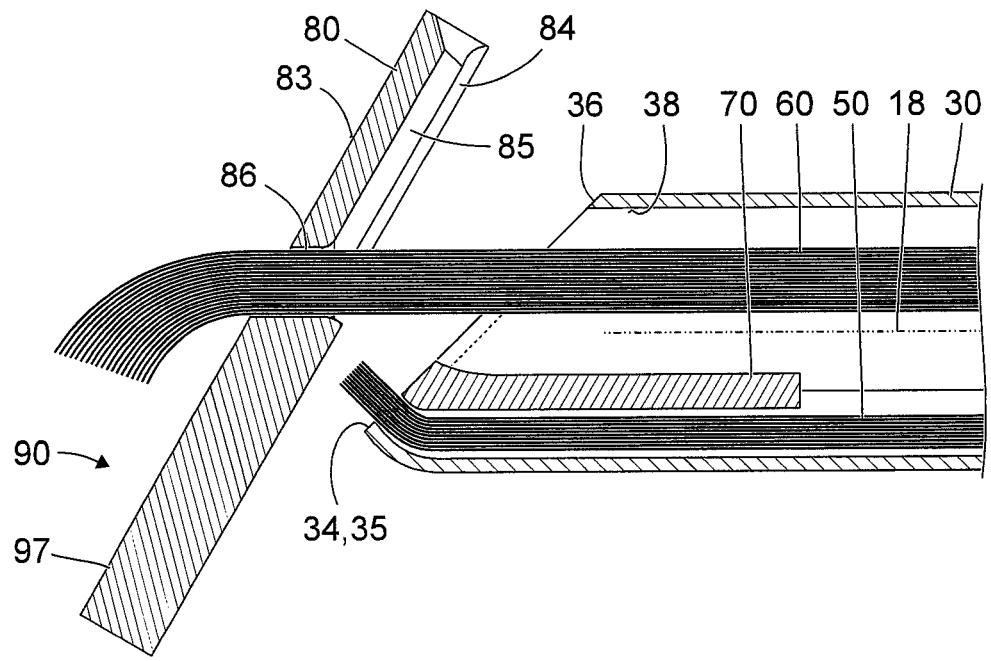
FIG. 8 shows a further schematic representation of a section through the distal end shown in FIGS. 3 through 7.

FIG. 8 shows a further schematic sectional representation of components of the distal end 22 of the shaft 20 described above with reference to FIGS. 1 through 6. The sectional plane of FIG. 8 is the sectional plane of FIGS. 3 through 7.

In the configuration shown in FIG. 8, the optics members 40, the first optical fibers 50 and the first segment 70 are in their predetermined final positions or almost in their predetermined final positions. The optics members 40 subdivide the lumen of the outer shaft member 30 into two compartments one of which accommodates the first optical fibers 50. The second optical fibers 60 are threaded through the second compartment and through a through hole 86 in a segment work piece 90. At the end of the manufacturing process, a proximal section (in the upper region of FIG. 8) of the segment work piece 90 will be the second segment 80. In other words, the segment work piece 90 comprises a proximal section which will form the second segment 80 at the end of the manufacturing process, whereas a proximal section 97 (in the lower left region of FIG. 8) of the segment work piece 90 will be removed (for instance milled off) before the end of the manufacturing process.

A concavely curved recess 84 corresponding to an outer surface region of a corresponding one of the optics members 40 and the above mentioned concavely curved recess 85 finally accommodating the second optical fibers 60 are visible in FIG. 8. A convexly curved surface area 83 averted from the recesses 84, 85 is provided for abutting on an inner surface region 38 of the outer shaft member 30.

Figure 9:
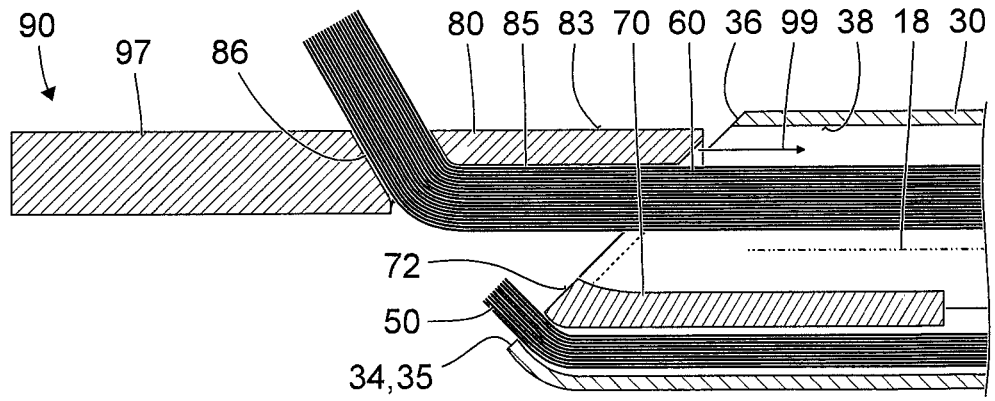
FIG. 9 shows a further schematic representation of a section through the distal end shown in FIGS. 3 through 8.

FIG. 9 shows another schematic sectional representation of components of the distal end 22 of the shaft 20 described above with reference to FIGS. 1 through 6. The sectional plane of FIG. 9 is the sectional plane of FIGS. 3 through 8.

In the configuration shown in FIG. 9, the segment work piece's 90 proximal part (which will finally form the second segment 80) is going to be inserted into the distal end 32 of the outer shaft member 30 in a second direction 99. The second direction 99 is opposite to the first direction 49 (confer FIG. 7) in which the optics members 40 are inserted into the outer shaft member 30.

Figure 10:
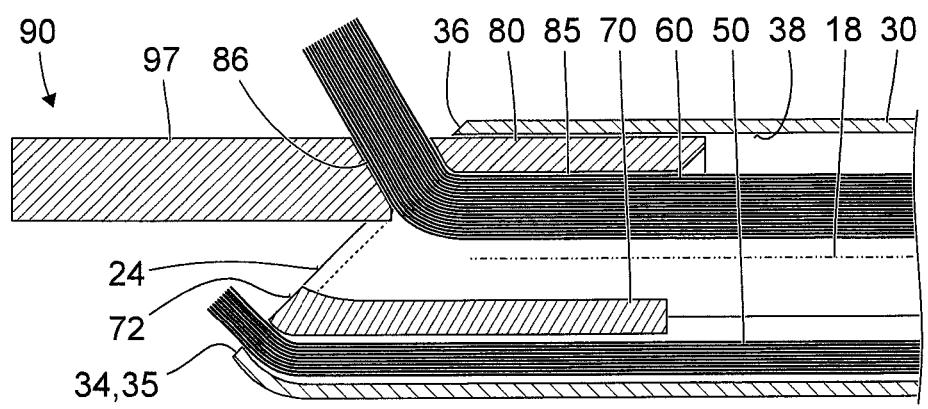
FIG. 10 shows a further schematic representation of a section through the distal end shown in FIGS. 3 through 9.

FIG. 10 shows another schematic sectional representation of components of the distal end 22 of the shaft 20 of the endoscope 10 described above with reference to FIGS. 1 through 6. The sectional plane of FIG. 10 is the sectional plane of FIGS. 3 through 9.

In the configuration shown in FIG. 10, the optics members 40, the optical fibers 50, 60, the first segment 70 and the segment work piece 90 are in their predetermined final positions relative to the outer shaft member 30. In this situation, an adhesive (or a casting or sealing compound) in a liquid phase is applied. Capillary action causes the liquid adhesive to fill all the gaps between the outer shaft member 30, the optics members 40, the optical fibers 50, 60, the first segment 70 and the segment work piece 90. When the adhesive is cured, it rigidly joins the optics members 40, the optical fibers 50, 60 (or, more precise, their respective distal ends 52, 62), the first segment 70 and the segment work piece 90 to each other and to the distal end of the outer shaft member 30. Thereby, the outer shaft member 30 is fluid tightly sealed. Thereafter, those parts of the optical fibers 50, 60 and of the segment work piece 90 protruding over the plane defined by the distal edge 34 of the outer shaft member 30 are removed and the distal front face 24 (confer FIGS. 2, 3) is polished.

Figure 11:
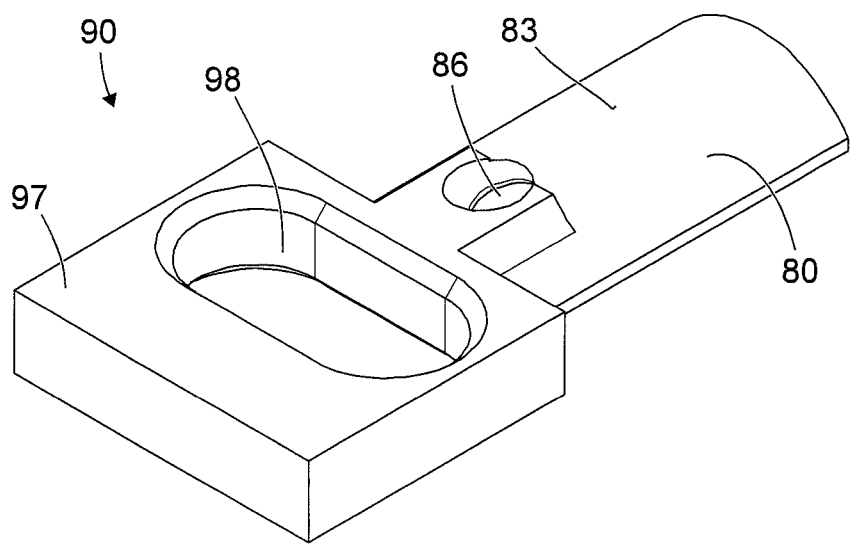
FIG. 11 shows a schematic axonometric representation of a segment work piece.

FIG. 11 shows a schematic axonometric representation of a segment work piece 90 similar to the segment work piece described above with reference to FIGS. 8 through 10.

The segment work piece 90 displayed in FIG. 11 differs from the segment work piece described above with reference to FIGS. 8 through 10 by a through hole 98 in the distal section of the segment work piece 90. The through hole 98 is provided for the accommodation of the first optical fibers 50, in particular in the situation shown in FIG. 10.

All the other features and characteristics of the segment work piece 90 displayed in FIG. 11 correspond to the features and characteristics of the segment work piece described above with reference to FIGS. 8 through 10. In particular, the segment work piece 90 displayed in FIG. 11 comprises a proximal section (in the above right part of FIG. 11) which will form the second segment 80 at the end of the manufacturing process. Said proximal section finally forming the second segment 80 comprises a convexly curved surface area 83 corresponding to an inner surface region 38 of an outer shaft member 30 (confer FIGS. 8, 9) the segment work piece 90 is made for. Furthermore, the segment work piece 90 comprises a through hole 86 made for the accommodation of distal ends of second optical fibers 60 (confer FIGS. 3 through 6 and 8 through 10).

Figure 12:
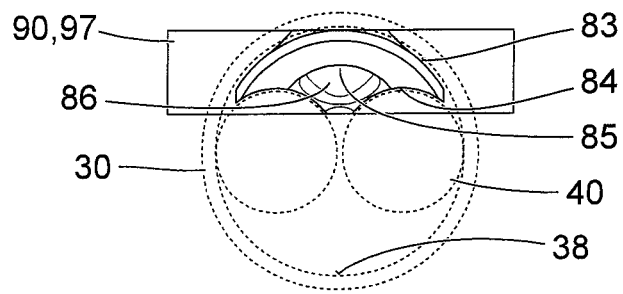
FIG. 12 shows a schematic representation of the segment work piece shown in FIG. 11.

FIG. 12 shows another schematic representation of the segment work piece 90 described above with reference to FIGS. 8 through 10 or the segment work piece described above with reference to FIG. 11; the only difference between both segment work pieces namely the through hole 98 in the distal section 97, is not visible in FIG. 12. The plane of projection of FIG. 12 is orthogonal to the planes of projection of FIGS. 1 and 2, orthogonal to the sectional plane of FIGS. 3 through 10, orthogonal to the longitudinal axis 18 of the shaft 20 and orthogonal to the directions 49, 99 (confer FIGS. 7, 9) in which the optics members 40 and the segment work piece 90 are to be inserted into the outer shaft member 30. In FIG. 12, the outer shaft member 30 and the optics members 40 are indicated with broken lines in their intended positions relative to the segment work piece 90.

As already mentioned above, the optics members 40 subdivide the lumen of the outer shaft member 30 into two separate compartments. The second segment 80 finally formed by the proximal section of the segment work piece 90 is accommodated in one of these two compartments. A convexly curved surface area 83 of the second segment 80 corresponds to the inner surface region 38 of the outer shaft member 30 and is provided to be joined to the corresponding inner surface region 38 of the outer shaft member 30. Concavely curved recesses 84 correspond to lateral surface regions of the optics members 40 and are provided for being joined to those lateral surface regions. The second segment's 80 concavely curved recess 85 forms a channel between the second segment 80 and the optics members 40, the distal end of which continuous to the through hole 86.

Figure 13:
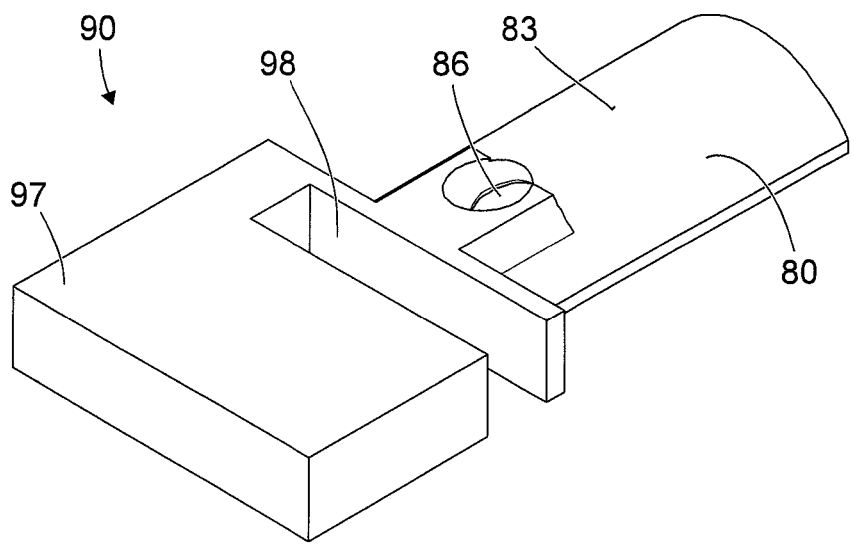
FIG. 13 shows a schematic representation of an alternative segment work piece.

FIG. 13 shows a schematic axonometric representation of another segment work piece 90. With respect to many features, characteristics and functions, the segment work piece 90 displayed in FIG. 13 is similar to the segment work pieces described above with reference to FIGS. 8 through 12.

The segment work piece 90 displayed in FIG. 13 differs from the segment work pieces described above with reference to FIGS. 8 through 11 in that a cut 98 rather than a through hole is provided in the distal section 97 of the segment work piece 90.

Figure 14:
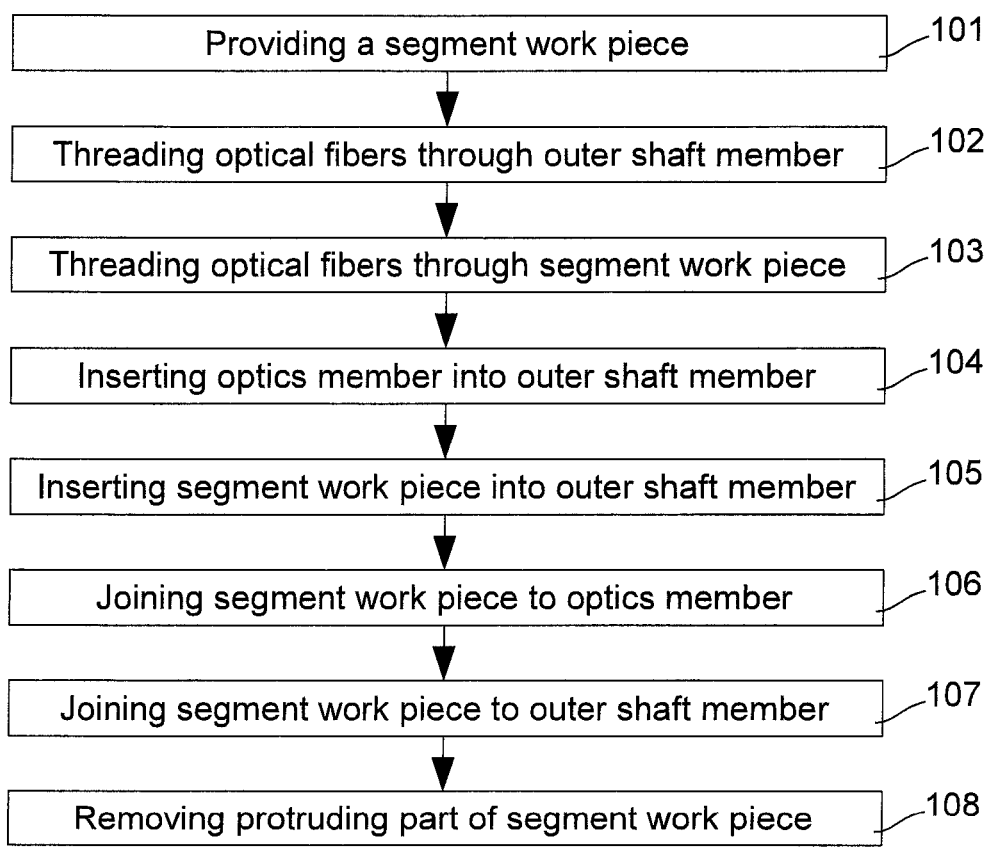
FIG. 14 shows a schematic flow chart of a method of manufacturing an endoscope.

FIG. 14 shows a schematic flow chart of a method of manufacturing an endoscope, in particular a distal end 22 of a shaft 20 of an endoscope 10 as described above with reference to FIGS. 1 through 13. Although the method described with reference to FIG. 14 can be applied for the manufacture of endoscopes with features, characteristics and functions different from those described above with reference to FIGS. 1 through 13, reference numerals of FIGS. 1 through 13 are used in an exemplary way for illustrative purposes only.

In a first step 101, a segment work piece 90 is provided. The segment work piece 90 comprises a proximal section to be inserted into the distal end 32 of an outer shaft member 30. The proximal section of the segment work piece will form a segment 80 at the end of the manufacturing process.

In a second step 102, optical fibers 60 are threaded through an outer shaft member 30. In a third step 103, the optical fibers 60 are threaded through a through hole 86 in the segment work piece 90. The second step 102 and the third step 103 can be conducted in this order or in the reverse order or simultaneously.

In a fourth step 104, an optics member 40 or two optics members 40 are inserted into the outer shaft member 30. In particular, the optics member 40 or the optics members 40 are inserted into the outer shaft member 30 in a first direction 49 from the proximal end to the distal end 32 of the outer shaft member 30. The fourth step 104 can be conducted before or after each of the second step 102 and the third step 103 or simultaneously with the third step 102 and/or with the third 103.

In a fifth step 105, the segment work piece 90, in particular its proximal section provided to finally form a segment 80, is inserted into the outer shaft member 30. In particular, the segment work piece 90 is inserted into the outer shaft member 30 in a second direction 99 opposite to the first direction 49. In particular, the fifth step 105 is conducted after the second step 102, the third step 103 and the fourth step 104. However, as an alternative, the fifth step 105 can be conducted before one or several of the other steps.

In a sixth step 106, the segment work piece 90 or at least its proximal section 80, is joined to the optics member 40 or to the optics members 40. In a seventh step 107, the segment work piece 90 or its proximal section 80 is joined to the outer shaft member 30. The sixth step 106 and the seventh step 107 can be conducted simultaneously or in any order. In particular, each of the sixth step 106 and the seventh step 107 is conducted by applying a liquid adhesive which, due to capillary action, fills all gaps at the distal end 22 of the shaft 20 before it is cured.

In an eighth step 108, a protruding part 97 of the segment work piece 90 is removed. Simultaneously protruding parts of optical fibers 50, 60 or of other components can be removed. Finally, the distal front face 24 of the shaft 20 can be polished.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. An endoscope comprising:
   an outer shaft member with a distal end forming a distal end of the endoscope;
   an optics member with a distal end, the optics member being located inside the outer shaft member, the optics member defining a viewing direction of the endoscope, the viewing direction being tilted relative to a longitudinal axis of the outer shaft member;
   a first bundle of optical fibers comprising an optically transparent material and provided and conditioned for the transport of illumination light to the distal end of the endoscope; and
   a first segment portion and a second segment portion, that are separate and discontinuous from each other, and disposed, respectively, between opposite sides of the optics member and opposite sides of an inner surface of the outer shaft member,
   wherein an orientation of distal ends of the first bundle of optical fibers is defined by at least one of the first segment portion and the second segment portion.

2. The endoscope according to claim 1, wherein a distal front face of the endoscope is tilted, wherein the edge of the distal front face of the endoscope provides a most distal region and a most proximal region, wherein the distal ends of the first bundle of optical fibers are located between the distal end of the optics member and the most proximal region of the edge of the distal front face of the endoscope.

3. The endoscope according to claim 1, further comprising a second bundle of optical fibers disposed separately and apart from the first bundle of optical fibers, the second bundle of optical fibers comprising an optically transparent material and provided and conditioned for the transport of illumination light to the distal end of the endoscope, wherein distal ends of the second bundle of optical fibers are located between the distal end of the optics member and the most distal region of the edge of the distal front face of the endoscope.

4. The endoscope according to claim 1, wherein the distal end of the optics member directly abuts on and/or is directly joined to the distal end of the outer shaft member.

5. The endoscope according to claim 1, wherein the distal end of the optics member directly abuts on and/or is directly joined to two separate regions of the inner surface of the distal end of the outer shaft member.

6. The endoscope according to claim 1, wherein the endoscope is a stereo-endoscope comprising two optical paths for the capture of two pictures facilitating binocular vision.

7. The endoscope according to claim 6, wherein the endoscope comprises two optics members arranged in parallel, each optics member providing one of the optical paths, and wherein at least one distal end of the optics member directly abuts on and/or is directly joined to the distal end of the outer shaft member.

8. The endoscope according to claim 1, wherein the first segment portion and the second segment portion do not completely surround the distal end of the optics member.

9. The endoscope according to claim 1, wherein adhesive or solder or a sealing or casting compound or a weld or a crimp joins at least one of the first segment portion and the second segment portion to at least one of the outer surface region of the distal end of the optics member and the inner surface region of the distal end of the outer shaft member.

10. The endoscope according to claim 1, wherein at least one of the first segment portion and the second segment portion comprises a through hole accommodating the distal ends of the first bundle of optical fibers.

11. The endoscope according to claim 10, wherein the orientation of the through hole defines the orientation of the distal ends of the first bundle of optical fibers, and wherein the orientation of the through hole is tilted relative to the longitudinal axis of the endoscope.

12. An endoscope comprising:
   an outer shaft member with a distal end forming a distal end of the endoscope;

an optics member with a distal end, the optics member being located inside the outer shaft member, the optics member defining a viewing direction of the endoscope, the viewing direction being tilted relative to a longitudinal axis of the outer shaft member;

optical fibers comprising an optically transparent material and provided and conditioned for the transport of illumination light to the distal end of the endoscope;

a first segment portion and a second segment portion that are separate and discontinuous from each other and that are disposed, respectively, between opposite sides of the optic member and opposite sides of an inner surface of the outer shaft member; and a distal front face tilted relative to the longitudinal axis of the outer shaft member, wherein the orientation of distal ends of the optical fibers is defined by at least one of the first segment portion and the second segment portion, wherein the edge of the distal front face of the endoscope provides a most distal region and a most proximal region, and wherein each of the first segment portion and the second segment portion are located between the distal end of the optics member and the most proximal region of the edge of the distal front face of the endoscope.

13. A method of manufacturing an endoscope, the method comprising:

providing a first segment portion and a second segment portion that are separate and discontinuous from each other, the second segment portion having a through hole;

threading optical fibers through the through hole in the second segment portion;

inserting an optics member into an outer shaft member of the endoscope; and inserting the first segment portion and the second segment portion to abut on opposite sides of an inner surface of the outer shaft member.

14. The method according to claim 13, wherein the optics member is inserted into the outer shaft member in a first direction from a proximal end of the outer shaft member to the distal end of the outer shaft member, and wherein the first segment portion and the second segment is portion are inserted into the outer shaft member in a second direction opposite to the first direction.

15. The method according to claim 13, further comprising:

simultaneously joining one of the first segment portion and the second segment portion to an outer surface region of a distal end of the optics member and to an inner surface region of a distal end of the outer shaft member.

16. The method according to claim 15, further comprising threading the optical fibers through the outer shaft member of the endoscope between the first segment portion and an inner surface of the outer shaft member.

17. The method according to claim 13, further comprising:

removing a region of the second segment portion protruding from the distal end of the outer shaft member.

18. The method according to claim 13, further comprising:

threading the optical fibers through the outer shaft member of the endoscope before or after threading the optical fibers through the through hole in the second segment portion.

19. The method according to claim 13, further comprising threading the optical fibers through the outer shaft member of the endoscope between the first segment portion and the inner surface of the outer shaft member.

20. The method according to claim 19, further comprising providing a second optics members arranged in parallel with the optics member to form two optical paths, wherein at least one distal end of the optics member is connected to directly abut on or is directly joined to the distal end of the outer shaft member.

\* \* \* \* \*